United States Patent [19]

Blank et al.

[11] Patent Number: 4,865,844

[45] Date of Patent: Sep. 12, 1989

[54] METHOD OF TREATING TINEA PEDIS AND RELATED DERMATOPHYTIC INFECTIONS

[75] Inventors: Lynne B. Blank, Brighton, N.Y.; Richard L. Gettings, Freeland; William C. White, Midland, both of Mich.

[73] Assignee: Dow Corning Corporation, Midland, Mich.

[21] Appl. No.: 196,405

[22] Filed: May 20, 1988

[51] Int. Cl.$^4$ ............... A01N 25/08; A01N 25/34; A01N 25/00; A61K 31/78

[52] U.S. Cl. ............... 424/409; 424/404; 424/78; 424/81; 424/405; 514/944; 514/937; 514/969; 514/938; 514/63; 514/858; 523/122

[58] Field of Search ............... 514/63, 858; 424/409, 424/81, 404, 78, 405, 944; 523/122

[56] References Cited

U.S. PATENT DOCUMENTS

| | | | |
|---|---|---|---|
| 3,560,385 | 2/1971 | Roth | 252/49.6 |
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/169 |
| 3,896,220 | 7/1975 | Shapiro | 514/150 |
| 4,097,590 | 6/1978 | Weisz | 252/106 |
| 4,201,765 | 5/1980 | Sichak | 424/45 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 514/63 |
| 4,395,454 | 7/1983 | Baldwin | 428/290 |
| 4,406,892 | 9/1983 | Eudy | 424/184 |
| 4,408,996 | 10/1983 | Baldwin | 8/490 |
| 4,411,928 | 10/1983 | Baldwin | 427/2 |
| 4,414,268 | 11/1983 | Baldwin | 428/289 |
| 4,425,372 | 1/1984 | Baldwin | 427/2 |
| 4,467,013 | 8/1984 | Baldwin | 428/289 |
| 4,504,541 | 3/1985 | Yasuda et al. | 428/264 |
| 4,567,039 | 1/1986 | Stadnick et al. | 424/70 |
| 4,615,937 | 10/1986 | Bouchette | 428/288 |
| 4,631,297 | 12/1986 | Battice et al. | 521/78 |
| 4,692,374 | 9/1987 | Bouchette | 428/288 |
| 4,721,511 | 1/1988 | Kupits | 8/188 |

FOREIGN PATENT DOCUMENTS

| | | | |
|---|---|---|---|
| 156809 | 3/1985 | Japan . | |
| WO79/00454 | 7/1979 | PCT Int'l Appl. | 514/63 |
| WO86/01457 | 1/1987 | PCT Int'l Appl. . | |
| 1386876 | 3/1975 | United Kingdom . | |
| 1433303 | 4/1976 | United Kingdom . | |
| 2155337 | 9/1985 | United Kingdom | 514/63 |

*Primary Examiner*—Joseph L. Schofer
*Assistant Examiner*—Carmen Pili-Curtis
*Attorney, Agent, or Firm*—Jim DeCesare

[57] ABSTRACT

A therapeutic method of treating the chronic human superficial fungus infection tinea pedis produced by the pathogenic dermatophytic fungi Microsporum sp., Trichophyton sp., and Epidermophyton sp., which invade and attack keratinized skin areas of the body by repeatedly applying topically to the itching, macerated, cracked, and scaling skin areas of the body at the site of the infection a fungicidally effective amount of a silane-containing lotion antagonistic to the dermatophytic fungi in order to exert at least an inhibitory growth effect upon the dermatophytes.

6 Claims, No Drawings

METHOD OF TREATING TINEA PEDIS AND RELATED DERMATOPHYTIC INFECTIONS

BACKGROUND OF THE INVENTION

This invention relates to a therapeutic method of treating the chronic human superficial fungus infection tinea pedis produced by the pathogenic dermatophytic fungi Microsporum sp., Trichopyton sp., and Epidermophyton sp., which invade and attack keratinized skin areas of the body, by repeatedly applying topically to the itching, macerated, cracked, and scaling skin areas of the body at the site of the infection a fungicidally effective amount of a lotion antagonistic to the dermatophytic fungi in order to exert at least an inhibitory growth effect upon the dermatophytes, the lotion including an antimicrobially active silane which is a quaternary ammonium salt.

Antimicrobial agents are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. Of the diverse categories of antimicrobial agents and compositions, quaternary ammonium compounds represent one of the largest of the classes of antimicrobial agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Non-silicone quaternary antimicrobials are not known to be or taught to be effective against dermatophytic fungi and in fact are known not to be effective in such uses because of interferences caused by the organic matter present on skin specifically the active infection sites. Silicone quaternary ammonium salt compounds are well known as exemplified by U.S. Pat. No. 3,560,385, issued Feb. 2, 1971, and the use of such compounds as antimicrobial agents is taught, for example, in a wide variety of patents such as U.S. Pat. No. 3,730,701, issued May 1, 1973, and 3,817,739, issued June 18, 1974, where the compounds are used to inhibit algae; 3,794,736, issued Feb. 26, 1974, and 3,860,709, issued Jan. 14, 1975, where they are employed for sterilizing or disinfecting a variety of surfaces and instruments; 3,865,728, issued Feb. 11, 1975, where the compounds are used to treat aquarium filters; 4,259,103, issued Mar. 31, 1981; and in British Pat. No. 1,386,876, of Mar. 12, 1975. Published unexamined European application No. 228464 of July 15, 1987, teaches the microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366, issued Aug. 4, 1981. In U.S. Pat. No. 4,504,541, issued Mar. 12, 1985, an antimicrobial fabric is disclosed which is resistant to discoloration and yellowing by treatment of the fabric with a quaternary ammonium base containing an organosilicone. U.S. Pat. No. 4,615,937, issued Oct. 7, 1986, as well as its companion U.S. Pat. No. 4,692,374, issued Sept. 8, 1987, relate to wet wiper towelettes having an antimicrobial agent substantive to the fibers of the web and being an organosilicon quaternary ammonium compound. In a series of Burlington Industries, Inc. U.S. Pat. Nos. 4,408,996, issued Oct. 11, 1983, 4,414,268, issued Nov. 8, 1983, 4,425,372, issued Jan. 10, 1984, and 4,395,454, issued July 26, 1983, such compounds are disclosed to be useful in surgical drapes, dressings, and bandages. This same assignee also discloses these compounds as being employed in surgeons' gowns in U.S. Pat. Nos. 4,411,928, issued Oct. 25, 1983, and 4,467,013, issued Aug. 21, 1984. Organosilicon quaternary ammonium compounds have been employed in carpets, in U.S. Pat. No. 4,371,577, issued Feb. 1, 1983; applied to walls, added to paints, and sprayed into shoes, in U.S. Pat. No. 4,394,378, issued July 19, 1983; applied to polyethylene surfaces and used in pillow ticking in U.S. Pat. No. 4,721,511, issued Jan. 26, 1988; in flexible polyurethane foams of fine-celled, soft, resilient articles of manufacture in U.S. Pat. No. 4,631,297, issued Dec. 23, 1986; and mixed with a surfactant in Japanese Kokai application No. 58-156809, filed Aug. 26, 1983, of Sanyo Chemical Industries, Ltd., for the purpose of achieving uniformity of distribution of the compounds to a surface. Thus, the versatility of such compositions is readily apparent. However, no one, as far as is known, has used an organosilicon quaternary ammonium compound in lotion form in order to provide a topical skin application for the treatment of diseases such as tinea pedis. This infection has typically been treated with such compositions as morpholine hydroperfiodide as evidenced by U.S. Pat. No. 2,290,710; griseofulyin antifungous antibiotic drug; and a combination of undecylenic acid and zinc undecylenate. Therefore, in accordance with the present invention, it has been found that compositions which are antimicrobial can be formed in soothing lotion form and since they possess the characteristics and advantages of the silicone quaternary ammonium salts can be used to effectively treat skin infections such as tinea pedis. It has been further shown that substrates treated with organosilicon quaternary ammonium compounds provide for protection against organisms known to cause tinea pedis, tinea corpus and tinea captis. Thus, the compositions of the present invention act in preventing microbiological contamination and deterioration. For example, 3-(trimethoxysilyl)-propyldimethyloctadecylammonium chloride, hereinafter referred to as TMS, is an effective antimicrobial agent in which the active ingredient reacts with substrates with which it is brought into contact. These substrates demonstrate nonleaching broad spectrum antimicrobial activity. By including an antimicrobial component in the lotion composition, a convenient delivery system is realized. Hence, the compositions set forth in the present invention possess unique features and advantages over existing antimicrobial treating agents and provide improved results thereover. Thus, the disadvantages of the prior art are overcome with the present invention wherein improved antimicrobial agents are provided.

SUMMARY OF THE INVENTION

This invention relates to a therapeutic method of treating the chronic human superficial fungus infection tinea pedis, tinea corpus, and tinea captis, produced by the pathogenic dermatophytic fungi Microsporum sp., Trichopyton sp., and Epidermophyton sp., which invade and attack keratinized skin areas of the body by repeatedly applying topically to the itching, macerated, cracked, and scaling skin areas of the body at the site of the infection a funcicidally effective amount of a lotion antagonistic to the dermatophytic fungi in order to exert at least an inhibitory growth effect upon the dermatophytes, the lotion including a silane of the general formula $$Y_3SiRN+R'R''R'''X-$$

where y denotes an organic or a hydrolyzable radical, R denotes a divalent hydrocarbon radical with 1 to 6 carbon atoms, R', R'' and R''' independently denote saturated or unsaturated hydrocarbon radicals containing 1 to 18 carbon atoms, saturated or unsaturated organic radicals consisting of carbon, hydrogen and oxygen; carbon, hydrogen, and sulfur; or carbon, hydrogen and nitrogen, and X denotes an anion.

The silane can also be represented by the general formula $$Y_3Si(CH_2)_mN+(CH_3)_2(CH_2)_nCH_3X-$$

where Y denotes an organic or a hydrolyable radical, X denotes an acid anion, and where m+n is 16 to 23, m is 1 to 11, and n is 9 to 17. Examples of preferred silane compounds for use in the present invention are represented by the formulae $$(CH_3O)_3Si(CH_2)_3N+(CH_3)_2C_{18}H_{37}Cl-$$

$$(CH_3O)_3Si(CH_2)_3N+(C_{10}H_{21})_2(CH_3)cl-$$

In a first embodiment, the lotion includes in addition to the silane each of talc, triethanolamine, propylene glycol, a suspension agent of a polymer of acrylic acid cross-linked with allyl sucrose, water, glyceryl stearate, lanolin alcohol, mineral oil, and stearic acid, whereas in a second embodiment, the lotion includes in addition to the silane each of methyl cellulose, talc, propylene glycol, water, glyceryl stearate, lanolin alcohol, mineral oil, stearic acid, and a low viscosity fluid blend of polydimethylcyclosiloxanes.

The invention also relates to a therapeutic composition for treating the chronic human superficial fungus infection tinea pedis, tinea captis, and tinea corpus, produced by the pathogenic dermatophytic fungi Microsporum sp., Teichophyton sp., and epidermophyton sp., which invade and attack keratinized skin areas of the body, for repeated application topically to the itching, macerated, cracked, and scaling skin areas of the body at the site of the infection, and being a fungicidally effective lotion antagonistic to the dermatophytic fungi for exerting at least an inhibitory growth effect upon the dermatophytes, the lotion including a silane of the general formula $$Y_3SiRN+R'R''R'''X-$$

where y denotes an organic or a hydrolyzable radical, R denotes a divalent hydrocarbon radical with 1 to 6 carbon atoms, R', R'' and R''' independently denote saturated or unsaturated hydrocarbon radicals containing 1 to 18 carbon atoms, saturated or unsaturated organic radicals consisting of carbon, hydrogen and oxygen; carbon, hydrogen, and sulfur; or carbon, hydrogen and nitrogen, and X denotes an anion.

It is therefore an object of the present invention to provide a lotion system containing a silane which is effective on skin against microbial conditions such as tinea pedis, tinea captis, and tinea corpus.

These and other objects, features, and advantages, of the present invention will become apparent from the following detailed description of the invention.

DETAILED DESCRIPTION OF THE INVENTION

Tinea pedis or dermatohytosis is a chronic superficial ringworm fungal infection of the skin. It is caused by the species of dermatophyte genera Trichophyton, Epidermophyton, and Microsporum. Although tinea pedis may be of different types and degrees of severity, it is marked by maceration, cracking, and scaling of the skin, and by intense itching. It has been found that certain lotions containing silanes when prepared and applied in accordance with the teachings of the present invention, however, are effective to inhibit the growth, spread, and reoccurrence of the tinea pedis disease, and effectively combat the tinea pedis infection, as well as tinea captis and tinea corpus which are caused by the same species of dermatophyte genera.

The lotion compositions of the present invention were prepared in accordance with the Examples set forth hereinbelow, and in the Examples as well as in the Tables tabulating results thereof, the composition identified as TMS refers to a product manufactured by the Dow Corning Corporation as an antimirobial agent and is 3-(trimethoxysilyl)-propyloctadecyldimethyl ammonium chloride diluted to forty-two percent active ingredients by weight with methanol, and having the formula $$(CH_3O)_3Si(CH_2)_3N+(CH_3)_2C_{18}H_{37}Cl-$$

The anion of an aqueous sodium salt of bromphenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple.

The blank solution is adjusted to yield a 10 to 12% transmittance reading when measured in 1 cm cells using a spectrophotometer set at 589 nm by the following method.

Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, PA, USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1 % are read spectophotometrically and a curve is plotted.

The silanes useful in this invention have the general formula

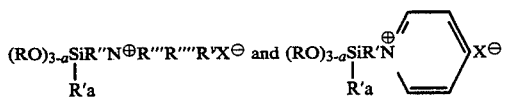

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R Malek and John L. Speier, on Mar. 31, 1981, discusses the use of such silanes to render the surfaces of certain substrates antimicrobial. Canadian Pat. No. 1,010,782, issued to Charles A. Roth shows the use of fillers treated with certain silanes to be used in paints and the like to give antimicrobial effects.

Numerous other publications have disclosed such silanes, namely, A. H. Isquith, E. A. Abbott and P. A. Walters, Applied Microbiology, December, 1972, pages 859-863; P. A. Walters, E. A. Abbott and A. J. Isquith, Applied Microbiology, 25, No. 2, p. 253-256, February 1973 and E. A. Abbott and A. J. Isquith, U.S. Pat. No. 3,794,736 issued Feb. 26, 1974, U.S. Pat. No. 4,406,892, issued Sept. 27, 1983, among others.

For purposes of this invention, the silanes can be used neat or they can be used in solvent or aqueous-solvent solutions. When the silanes are used neat, the inventive process is preferably carried out in a system in which some small amount of water is present. It it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the ≡SiOH that is formed by hydrolysis of the alkoxy groups present on the silane. The ≡SiOH groups tend to react with the surface and bind the silane to the surface. It is believed by the inventor even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. In the above formulas RO can also be R. R can also be hydrogen thus indicating the silanol form, i.e. the hydrolyzate. The value of a is 0, 1 or 2 R' is methyl or ethyl radical.

R" for purposes of this invention is an alkylene group of 1 to 4 carbon atoms. Thus, R" can be alkylene groups such as methylene, ethylene, propylene, and butylene. R''', R'''', and R$^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$. x has a value of from 2 to 10 and R$^{vi}$ is a perfluoroalkyl radical having from 1 to 12 carbon atoms. X is chloride, bromide, fluoride, iodide, acetate or tosylate.

Preferred for this invention are the silanes of the general formula

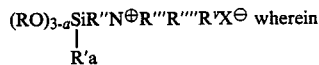 wherein

R is methyl or ethyl; a has a value of zero; R" is propylene; R''' is methyl or ethyl; R'''' and R$^v$ are selected from alkyl groups containing 1 to 18 carbon atoms wherein at least one such group is larger than eight carbon atoms and x is either chloride, acetate or tosylate.

Most preferred for this invention are those silanes having the formula

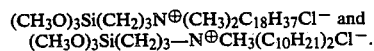

As indicated above, most of these silanes are known from the literature and methods for their preparation are known as well. See, for example, U.S. Pat. No. 4,282,366, issued Aug. 4, 1981; U.S. Pat. No. 4,394,378, issued July 19, 1983, and U.S. Pat. No. 3,661,963 issued May 9, 1972, among others.

Specific silanes within the scope of the invention are represented by the formulae:

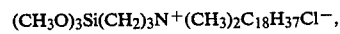

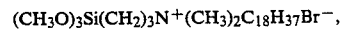

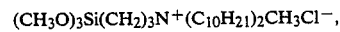

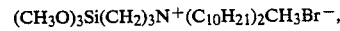

$(CH_3O)_3Si(CH_2)_3N^+(CH_3)_3Cl^-$, $(CH_3O)_3SiCH_2CH_2CH_2P^+(C_6H_5)_3Cl^-$, $(CH_3O)_3SiCH_2CH_2CH_2P^+(C_6H_5)_3Br^-$, $(CH_3O)_3SiCH_2CH_2CH_2P^+(CH_3)_3Cl^-$, $(CH_3O)_3SiCH_2CH_2CH_2P^+(C_6H_{13})_3Cl^-$, $(CH_3)_3Si(CH_2)_3N^+(CH_3)_2C_{12}H_{25}Cl^-$, $(CH_3)_3Si(CH_2)_3N^+(C_{10}H_{21})_2CH_3Cl^-$, $(CH_3)_3Si(CH_2)_3N^+(CH_3)_2C_{18}H_{37}Cl^-$, $(CH_3O)_3Si(CH_2)_3N^+(CH_3)_2C_4H_9Cl^-$, $(C_2H_5O)_3Si(CH_2)_3N^+(CH_3)_2C_{18}H_{37}Cl^-$, $(CH_3O)_3Si(CH_2)_3N^+(CH_3)_2CH_2C_6H_5Cl^-$, $(CH_3O)_3Si(CH_2)_3N^+(CH_3)_2CH_2CH_2OHCl^-$,

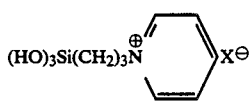

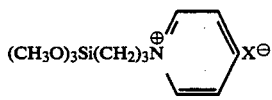

$(CH_3O)_3Si(CH_2)_3N^+(CH_3)_2(CH_2)_3NH\text{-}C(O)(CF_2)_6CF_3Cl^-$, $(CH_3O)_3Si(CH_2)_3N^+(C_2H_5)_3Cl^-$.

Lotion systems of TMS were prepared and shown to be effective on sking against the microbial condition tinea pedis, tinea corpus, and tinea captis. The antimicrobial material was incorporated into lotion formulations and shown to reduce the tinea pedis, tinea corpus, and tinea captis infections.

EXAMPLE I

A control lotion and a lotion containing antibacterial agent were each prepared by placing in a container each of the ingredients identified below in Table I as batch A. These materials were used in amounts corresponding to the weight percentages shown in Table I. The material CARBOMER ®941 is a suspension agent of a polymer of acrylic acid cross-linked with allyl sucrose and sold by B. F. Goodrich Chemical Company. The batch A materials were mixed together until a consistency developed. Into a separate container was placed each of the ingredients identified below in Table I as batch B. These materials were used in amounts corresponding to the weight percentages shown in Table I. The batch B materials were mixed together until a consistency developed. The materials of batches A and B were combined in a separate container and mixed for four minutes on an Eppenback mechanical mixer at thirty volts variac. A creamy lotion resulted. In order to show the efficacy of the lotion, it is again noted that the anion of the aqueous sodium salt os bromophenol blue dye complexes with the cation of polymerized TMS on a given substrate. The dye was prepared by dissolving 0.02 percent of bromophenol blue in distilled water and rendering the solution slightly alkaline with a few drops of saturated sodium carbonate per one hundred milliliters of solution. The creamy antimicrobial agent containing lotion was rubbed into a sheet of fabric, and left a substantive blue stain when two to three drops of the bromophenol blue solution was added to the fabric and rinsed with water. In order to show the efficacy of the foregoing lotion on skin, the subject skin substrate was washed with soap and water. The antimicrobial agent containing creamy lotion was applied to the skin and rubbed in thoroughly until completely absorbed. A tape pull test was performed in order to determine the dermal penetration of the lotion by applying to the treated skin area a one milliliter aliquot of bromophenol blue standard solution. The dye was rubbed around the treated area, rinsed with water and dried. A section of 3M SCOTCH® brand tape was applied over the treated skin area and rubbed in to insure good adhesion. The tape was then removed by one quick pull. This procedure was repeated on the same treated skin area until no blue color was detectable when the tape section was placed on a sheet of white paper. It was found that six tape pulls were required to remove all traces of blue stain from the stratum corneum. Thus, the antimicrobial lotion penetrated the upper dead layers of skin where conditioning and protection were needed, but the lotion did not pass into the body. Use tests indicated that with repeated application of the antimicrobial lotion to the effected area over a period of time, that the symptoms disappeared in about two days.

EXAMPLE II

Three antimicrobial lotions were prepared by combining in separate containers each of the ingredients identified below in Table II as batch A. These materials were used in amounts corresponding to the weight percentages shown in Table II. The material identified as PDMCS is a product of Dow Corning Corporation and a low viscosity fluid blend of polydimthylcyclosiloxanes. The batch A materials were mixed together and heated until melted. Into a separate container was placed each of the ingredients identified below in Table II as batch B. These materials were used in amounts corresponding to the weight percentages shown in Table II. The batch B materials were mixed together and heated until melted. The materials of batches A and B were combined in a separate container and mixed for four minutes on an Eppenbach mechanical mixer at thirty volts variac. A creamy lotion resulted in each case. As in Example I, the anion of the aqueous sodium salt of bromophenol blue dye complexes with the cation of polymerized TMS on a given substrate. The dye was prepared by dissolving 0.02 percent of bromophenol blue in distilled water and rendering the solution slightly alkaline with a few drops of saturated sodium carbonate per one hundred milliliters of solution. The creamy antimicrobial agent containing lotions were rubbed into a sheet of fabric, and left a substantive blue stain when two to three drops of the bromophenol blue solution was added to the fabric and rinsed with water. In order to show the efficacy of the foregoing lotions on skin, the subject skin substrate was washed with soap and water. The antimicrobial agent containing creamy lotions were applied to the skin and rubbed in thoroughly until completely absorbed. A tape pull test was performed in order to determine the dermal penetration of the lotions by applying to the treated skin area a one milliliter aliquot of bromophenol blue standard solution. The dye was rubbed around the treated area, rinsed with water and dried. A section of 3M SCOTH® brand tape was applied over the treated skin area and rubbed in to insure good adhesion. The tape was then removed by one quick pull. This procedure was repeated on the same treated skin area until no blue color was detectable when the tape section was placed on a sheet of white paper. It was found that six tape pulls were required to remove all traces of blue stain from the stratum corneum. Thus, the antimicrobial lotions penetrated the upper dead layers of skin where conditioning and protection were needed, but the lotions did not pass into the body. Use tests indicated that with repeated application of the antimicrobial lotions to the effected area over a period of time, that the symptoms disappeared in about two days. Thus, the lotions were considered effective against the microbial condition, and it was also noted that the lotions containing the antimicrobially active agent reduced the odor of perspiration associated with the microorganisms on the skin surface to which the lotion was applied.

TABLE I

| Lotion Formulations | | |
|---|---|---|
| | 5575-428-1C Control | 428-1 TMS |
| A. Talc | 0.5 | 0.5 |
| Triethanolamine | 0.5 | 0.5 |
| Propyleneglycol | 1.5 | 1.5 |
| Carbomer 941 | 0.5 | 0.5 |
| H$_2$O | 90.0 | 90.0 |
| B. TMS | 0.0 | 0.5 |
| Glyceryl Stearate | 0.5 | 0.5 |
| Lanolin Alcohol | 0.5 | 0.5 |
| Mineral Oil | 4.5 | 4.5 |
| Stearic Acid | 1.0 | 1.0 |

TABLE II

| Lotion Formulations | | | |
|---|---|---|---|
| | 428-2 | 504-1 | 727-1 |
| A. Methyl Cellulose | 6.0 | 6.0 | 6.0 |
| Talc | 1.5 | — | — |
| Propylene Glycol | 4.5 | 4.5 | 4.5 |
| H$_2$O | 270.0 | 270.0 | 270.0 |
| B. Glyceryl Stearate | 1.5 | 1.5 | — |
| Lanolin Alcohol | 1.5 | 1.5 | 1.5 |
| Mineral Oil | 10.0 | 15.0 | 15.0 |
| PDMCS | 5.0 | 2.0 | 2.0 |
| Stearic Acid | 3.0 | 3.0 | — |
| TMS | 2.0 | 2.0 | 5.0 (70% solids) |

The antimicrobial activity of a treated surface is evaluated by shaking a sample weighing 0.75 grams in a 750,000 to 1,500,000 count *Klebsiella pneumoniae* suspension for a one hour contact time. The suspension is serially diluted, both before and after contact, and cultured. The number of viable organisms in the suspensions is determined. The percent reduction based on the original count is determined. The method is intended for those surfaces having a reduction capability of 75 to 100% for the specified contact time. The results are reported as the percent reduction.

Media used in this test are nutrient broth, catalog No. 0003-01-6 and tryptone glucose extract agar, catalog No. 0002-01-7 both available from Difco Laboratories, Detroit, Mich., U.S.A. The microorganism used is *Klebsiella pneumoniae* American Type Culture Collection; Rockville, Md. U.S.A., catalog No. 4352.

The procedure used for determining the zero contact time counts is carried out by utilizing two sterile 250 ml. screw-cap Erlenmeyer flasks for each sample. To each flask is added 70 ml of sterile buffer solution. To each flask is added, aseptically, 5 ml of the organism inoculum. The flasks are capped and placed on a wrist action shaker. They are shaken at maximum speed for 1 minute. Each flask is considered to be at zero contact time and is immediately subsampled by transferring 1 ml of each solution to a separate test tube containing 9 ml of sterile buffer. The tubes are agitated with a vortex mixer and then 1 ml of each solution is transferred to a second test tube containing 9 ml of sterile buffer. Then, after agitation of the tubes, 1 ml of each tube is transferred to a separate sterile petri dish. Duplicates are also prepared. Sixteen ml of molten (42° C.) tryptone glucose extract agar is added to each dish. The dishes are each rotated ten times clockwise and ten times counterclockwise. The dishes are then incubated at 37° C. for 24 to 36 hours. The colonies are counted considering only those between 30 and 300 count as significant. Duplicate samples are averaged. The procedure used for determining the bacterial count after 1 hour is essentially the same as that used to determine the count at the zero contact time. The only difference is that pour plating is performed at the $10^0$ and $10^{-1}$ dilutions as well as at the $10^{-2}$ dilution. "Percent reduction" is calculated by the formula $$\% R = \frac{\frac{B+C}{2} - A_{100}}{\frac{B+C}{2}}$$

where A is the count per milliliter for the flask containing the treated substrate; B is zero contact time count per milliliter for the flask used to determine "A" before the addition of the treated substrate and C is zero contact time count per milliliter for the untreated control substrate. In Example III, the foregoing routine was varied as will be apparent.

EXAMPLE III

In order to demonstrate that surface treated with TMS are self-sanitizing against the fungus Trichophyton mentagrophytes, orlon-nylon, and nylon fabrics were treated with the antimicrobial agent as 0.5%–1.25% based on weight of fabric, and cotton-nylon fabric was treated at levels of 0.75%–1.5% based on weight of fabric. Three product samples representing three different batches one of which was at least sixty days old were used to chemically impregnate each representative fabric for the intended useful life which was determined to be based on the number of launderings of the treated material. The test and control fabrics were inoculated with the test organism. At representative time intervals of zero and twenty-four hours the viable organisms were eluded from fabric swatches by shaking in known amounts of liquid. The number of the viable organisms in that liquid was then determined and the percentage reduction by the treated fabric was calculated. Circular swatches of one and seven-eights inch diameter were used, and each swatch was padded with the inoculum to insure even distribution. The fungal counts from the treated and untreated fabrics are shown in Table III to V for the orlon-nylon, nylon, and cotton-nylon fabrics, respectively. The data show that the treated fabrics were self-sanitizing against the fungus as compared to the untreated fabrics through at least ten laundering cycles, and that there was a slight diminishing of activity after ten launderings using this modified test method for determining efficacy.

TABLE III

Antifungal Activity[1] of Orlon/Nylon Fabric Treated[2] With Dow Corning ® TMS

| Sample | Number of Launderings[3] | Fungal CFU/Sample at: "0" Time | Fungal CFU/Sample at: 24 Hours | Log Reduction[5] | Percent Reduction[5] |
|---|---|---|---|---|---|
| A | 0 | $1.53 \times 10^6$ | $<10^2$ | >4.2 | >99.99 |
| B | 0 | $1.39 \times 10^6$ | $<10^2$ | >4.2 | >99.99 |
| C[4] | 0 | $1.76 \times 10^6$ | $<10^2$ | >4.2 | >99.99 |
| Control | 0 | $1.70 \times 10^6$ | $2.91 \times 10^6$ | — | — |
| A | 5 | $1.58 \times 10^6$ | $<10^2$ | >4.2 | >99.99 |
| B | 5 | $1.64 \times 10^6$ | $1.10 \times 10^2$ | 4.16 | 99.99 |
| C | 5 | $1.49 \times 10^6$ | $1.25 \times 10^2$ | 4.10 | 99.99 |
| Control | 5 | $1.62 \times 10^6$ | $2.03 \times 10^6$ | — | — |
| A | 10 | $1.38 \times 10^6$ | $1.01 \times 10^3$ | 3.18 | 99.9 |
| B | 10 | $1.71 \times 10^6$ | $1.32 \times 10^3$ | 3.06 | 99.9 |
| C | 10 | $1.60 \times 10^6$ | $1.49 \times 10^3$ | 3.01 | 99.9 |
| Control | 10 | $1.39 \times 10^6$ | $1.98 \times 10^6$ | — | — |
| A | 20 | $1.37 \times 10^6$ | $2.11 \times 10^4$ | 1.86 | 98.6 |
| B | 20 | $1.44 \times 10^6$ | $1.81 \times 10^4$ | 1.92 | 98.8 |
| C | 20 | $1.79 \times 10^6$ | $2.46 \times 10^4$ | 1.79 | 98.4 |
| Control | 20 | $1.43 \times 10^6$ | $2.20 \times 10^6$ | — | — |
| A | 25 | $1.81 \times 10^6$ | $2.30 \times 10^5$ | 0.89 | 87.1 |
| B | 25 | $1.66 \times 10^6$ | $1.98 \times 10^5$ | 0.95 | 88.9 |
| C | 25 | $1.75 \times 10^6$ | $1.50 \times 10^5$ | 1.07 | 91.6 |
| Control | 25 | $1.91 \times 10^6$ | $2.83 \times 10^6$ | — | — |

NOTES:
[1] Antifungal activity against *Trichophyton mentagrophytes*.
[2] Fabric treated at 0.75% O.W.F.
[3] Laundered with AATCC detergent and rinsed 2 times in water.
[4] Sample C was a 60 day shelf-life sample.
[5] Log reduction and percent reduction were calculated for the treated samples (A, B, C) using the average "0" time counts for each set of laundering cycles.

TABLE IV

Antifungal Activity[1] of Nylon Fabric Treated[2] With Dow Corning ® TMS

| Sample | Number of Launderings[3] | Fungal CFU/Sample at: "0" Time | Fungal CFU/Sample at: 24 Hours | Log Reduction[5] | Percent Reduction[5] |
|---|---|---|---|---|---|
| A | 0 | $9.6 \times 10^5$ | $<10^2$ | >3.95 | >99.9 |
| B | 0 | $8.1 \times 10^5$ | $<10^2$ | >3.95 | >99.9 |
| C[4] | 0 | $8.9 \times 10^5$ | $<10^2$ | >3.95 | >99.9 |
| Control | 0 | $9.0 \times 10^5$ | $9.7 \times 10^5$ | — | — |
| A | 5 | $7.8 \times 10^5$ | $<10^2$ | >3.98 | >99.9 |
| B | 5 | $9.9 \times 10^5$ | $<10^2$ | >3.98 | >99.9 |
| C | 5 | $1.05 \times 10^6$ | $1.02 \times 10^2$ | 3.97 | >99.9 |
| Control | 5 | $1.01 \times 10^6$ | $9.5 \times 10^5$ | — | — |
| A | 10 | $6.9 \times 10^5$ | $1.15 \times 10^2$ | 3.86 | >99.9 |
| B | 10 | $9.3 \times 10^5$ | $5.4 \times 10^2$ | 3.19 | 99.9 |
| C | 10 | $8.5 \times 10^5$ | $2.91 \times 10^2$ | 3.46 | 99.9 |
| Control | 10 | $8.9 \times 10^5$ | $9.0 \times 10^5$ | — | — |
| A | 20 | $7.5 \times 10^5$ | $2.85 \times 10^4$ | 1.48 | 96.6 |
| B | 20 | $9.5 \times 10^5$ | $1.78 \times 10^4$ | 1.68 | 97.9 |
| C | 20 | $9.1 \times 10^5$ | $1.99 \times 10^4$ | 1.63 | 97.7 |
| Control | 20 | $7.9 \times 10^5$ | $8.6 \times 10^5$ | — | — |
| A | 25 | $8.4 \times 10^5$ | $9.1 \times 10^4$ | 1.01 | 90.2 |
| B | 25 | $1.02 \times 10^6$ | $9.6 \times 10^4$ | 0.99 | 89.7 |
| C | 25 | $9.1 \times 10^5$ | $1.02 \times 10^5$ | 0.96 | 89.0 |
| Control | 25 | $9.3 \times 10^5$ | $9.5 \times 10^5$ | — | — |

NOTES:
[1] Antifungal activity against *Trichophyton mentagrophytes*.
[2] Fabric treated at 0.75% O.W.F.
[3] Laundered with AATCC detergent and rinsed 2 times in water.
[4] Sample C was a 60 day shelf-life sample.
[5] Log reduction and percent reduction were calculated for the treated samples (A, B, C) using the average "0" time counts for each set of laundering cycles.

TABLE V

Antifungal Activity[1] of Nylon Fabric Treated[2] With Dow Corning ® TMS

| Sample | Number of Launderings[3] | Fungal CFU/Sample at: "0" Time | Fungal CFU/Sample at: 24 Hours | Log Reduction[5] | Percent Reduction[5] |
|---|---|---|---|---|---|
| A | 0 | $2.85 \times 10^6$ | $<10^2$ | >4.37 | >99.99 |
| B | 0 | $2.14 \times 10^6$ | $<10^2$ | >4.37 | >99.99 |
| C[4] | 0 | $2.30 \times 10^6$ | $10^2$ | 4.37 | >99.99 |

TABLE V-continued

Antifungal Activity[1] of Nylon Fabric Treated[2] With Dow Corning ® TMS

| Sample | Number of Launderings[3] | Fungal CFU/Sample at: "0" Time | Fungal CFU/Sample at: 24 Hours | Log Reduction[5] | Percent Reduction[5] |
|---|---|---|---|---|---|
| Control | 0 | $1.99 \times 10^6$ | $1.89 \times 10^6$ | — | — |
| A | 5 | $2.51 \times 10^6$ | $1.35 \times 10^2$ | 4.22 | 99.99 |
| B | 5 | $2.42 \times 10^6$ | $1.81 \times 10^2$ | 4.09 | 99.99 |
| C | 5 | $2.10 \times 10^6$ | $1.60 \times 10^2$ | 4.15 | 99.99 |
| Control | 5 | $2.38 \times 10^6$ | $2.36 \times 10^6$ | — | — |
| A | 10 | $1.98 \times 10^6$ | $1.78 \times 10^3$ | 3.10 | 99.9 |
| B | 10 | $2.25 \times 10^6$ | $2.85 \times 10^3$ | 2.90 | 99.87 |
| C | 10 | $2.06 \times 10^6$ | $2.01 \times 10^3$ | 3.05 | 99.9 |
| Control | 10 | $2.68 \times 10^6$ | $2.79 \times 10^6$ | — | — |
| A | 20 | $1.91 \times 10^6$ | $1.95 \times 10^4$ | 2.07 | 99.1 |
| B | 20 | $2.53 \times 10^6$ | $2.21 \times 10^4$ | 2.02 | 99.0 |
| C | 20 | $2.40 \times 10^6$ | $2.10 \times 10^4$ | 2.04 | 99.1 |
| Control | 20 | $2.33 \times 10^6$ | $2.41 \times 10^6$ | — | — |
| A | 25 | $2.60 \times 10^6$ | $2.72 \times 10^5$ | 0.95 | 88.6 |
| B | 25 | $2.51 \times 10^6$ | $2.50 \times 10^5$ | 0.98 | 89.5 |
| C | 25 | $2.19 \times 10^6$ | $1.99 \times 10^5$ | 1.08 | 91.7 |
| Control | 25 | $2.25 \times 10^6$ | $1.01 \times 10^7$ | — | — |

NOTES:
[1] Antifungal activity against *Trichophyton mentagrophytes*.
[2] Fabric treated at 1.0% O.W.F.
[3] Laundered with AATCC detergent and rinsed 2 times in water.
[4] Sample C was a 60 day shelf-life sample.
[5] Log reduction and percent reduction were calculated for the treated samples (A, B, C) using the average "0" time counts for each set of laundering cycles.

EXAMPLE IV

In order to further demonstrate the effectiveness of TMS against the fungus trichophyton mentagrophytes, various types of nylon surfaces were treated with the antimicrobial agent, and the results are tabulated in Tables VI to IX. Comparisons were made on untreated as well as treated surfaces, in order to show the effect of TMS in inhibiting and inactivating test bacilli applied to the surfaces. Four types of nylon material surfaces were selected for the tests, including a high-pile cut, a fine velour, a light loop fabric, and a heavy-duty loop fabric. Durability of treatment was shown by testing each surface type in its new condition, and after 7, 14, and 21, shampoo treatments. For the shampoo treatments, a commercial spray extraction device was used, and a non-bacterial shampoo having active groups of non-ionic surfactants and phosphates. Each test was repeated three times in order to verify the results obtained.

Test surfaces 50 mm×50 mm were used as bacilli carrier. To prewet the surface, the surface was immersed at 37° C. into a phosphate buffer solution, removed, placed between sterile filter papers in order to remove excess fluid, and placed in sterile Petri dishes. Test bacilli suspensions were obtained from a nutrient bouillon incubated for 18 hours at 37° C. and stirred at a frequency of 120 rpm by transferring 1 ml of culture bouillon into 9 ml of phosphate buffer. From this 1:10 dilution, a 1:100 dilution was made by placing 1 ml from the first dilution into 9 ml of phosphate buffer. Using the same procedure, a 1:1000 dilution of the suspension was formed. The 1:1000 dilution was used to inoculate the test pieces in sterile Petri dishes by applying 0.01 ml along each lateral edge and diagonally or a total of 0.05 ml of test bacilli suspension per bacilli carrier. The inoculated pieces were placed into sealed Petri dishes in an air-tight container which was filled to 10% of its volume with water and preheated to 37° C. Incubation of the test pieces was conducted at 37° C. in the container for 4 hours.

The bacilli carrier was removed from the container and placed into covered glasses with 200 ml capacity and filled with 100 ml of Letheen broth, and shaken for 10 minutes on a shaking device with a frequency of 180 rpm. Reisolation of the test bacilli was carried out by transferring 1 ml from the Letheen broth directly into a Petri dish followed by one dilution with Letheen broth 1:10 and 1:100. 1 ml of each of the dilutions was placed into a Petri dish and covered with bacilli nutrient Sabouraud dextrose agar. The incubation time was 12 weeks. The fungi culture was incubated in a climate-controlled chamber at temperatures of 22±1° C. and at a relative atmospheric humidity of 96±3%. Readings were conducted during the 1st, 6th and 12th week. A precise quantitative evaluation was impossible because of the biological properties of the fungi. Therefore, the percentage of surface growth on the fungi bacilli nutrient dishes was evaluated, and is reported in Tables VI to IX. In should be apparent from a consideration of Tables VI to IX that TMS treatments were not only effectual but durable since even the high number of shampoo treatments had no significant effect on bacilli reduction rates. There was no re-isolation of the fungi species in any test, even after incubating the counting plates for twelve weeks in a climate-controlled chamber. In the tables, the reduction of fungi growth is expressed as growth on a plate in percent of plate surface.

TABLE VI

FUNGI GROWTH REDUCTION OF TREATED AND UNTREATED HIGH-PILE CUT NYLON TEST SURFACES

| Shampoo Treatments | Incubation Time (weeks) | Untreated Run 1 | Untreated Run 2 | Untreated Run 3 | TMS Treated Run 1 | TMS Treated Run 2 | TMS Treated Run 3 |
|---|---|---|---|---|---|---|---|
| 0 | 1 | 100 | 100 | 100 | 0 | 0 | 0 |
|  | 6 | 100 | 100 | 100 | 0 | 0 | 0 |
|  | 12 | 100 | 100 | 100 | 0 | 0 | 0 |

TABLE VI-continued

FUNGI GROWTH REDUCTION OF TREATED AND
UNTREATED HIGH-PILE CUT NYLON TEST SURFACES

| Shampoo Treatments | Incubation Time (weeks) | Untreated | | | TMS Treated | | |
|---|---|---|---|---|---|---|---|
| | | Run 1 | Run 2 | Run 3 | Run 1 | Run 2 | Run 3 |
| 7 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 14 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 21 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |

TABLE VII

FUNGI GROWTH REDUCTION OF TREATED AND
UNTREATED NYLON FINE VELOUR TEST SURFACES

| Shampoo Treatments | Incubation Time (weeks) | Untreated | | | TMS Treated | | |
|---|---|---|---|---|---|---|---|
| | | Run 1 | Run 2 | Run 3 | Run 1 | Run 2 | Run 3 |
| 0 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 7 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 14 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 21 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |

TABLE VIII

FUNGI GROWTH REDUCTION OF TREATED AND
UNTREATED NYLON LIGHT LOOP FABRIC TEST SURFACES

| Shampoo Treatments | Incubation Time (weeks) | Untreated | | | TMS Treated | | |
|---|---|---|---|---|---|---|---|
| | | Run 1 | Run 2 | Run 3 | Run 1 | Run 2 | Run 3 |
| 0 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 7 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 14 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 21 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |

TABLE IX

FUNGI GROWTH REDUCTION OF TREATED AND
UNTREATED NYLON HEAVY-DUTY LOOP FABRIC TEST SURFACES

| Shampoo Treatments | Incubation Time (weeks) | Untreated | | | TMS Treated | | |
|---|---|---|---|---|---|---|---|
| | | Run 1 | Run 2 | Run 3 | Run 1 | Run 2 | Run 3 |
| 0 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 7 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 14 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |
| 21 | 1 | 100 | 100 | 100 | 0 | 0 | 0 |
| | 6 | 100 | 100 | 100 | 0 | 0 | 0 |
| | 12 | 100 | 100 | 100 | 0 | 0 | 0 |

While the foregoing is set forth as specific to TMS, it should be apparent that other compositions exhibiting antimicrobial activity are effective for the purposes of the present invention including, for example, mixtures in methanol of 3-chloropropyltrimethoxysilane and 3-(trimethoxysilyl)-propyloctadecyldimethyl ammonium chloride.

It should be noted that carriers in addition to lotions may be employed herein such as gels, powders, creams emulsions, microemulsions, and solvent solutions such as tinctures, of the active antimicrobial agent. In addition surfaces other than skin can be treated such as carpet; fabrics, for example socks, clothing, shoe inner liners, towels, bedding, upholstery, curtains, and draperies; as well as hard surfaces, for example walls, tables, ceilings, and furnishings.

It will be apparent from the foregoing that many other variations and modifications may be made in the structures, compounds, compositions, articles of manufacture, and methods described herein without departing substantially from the essential features and concepts of the present invention. Accordingly, it should be clearly understood that the forms of the invention described herein are exemplary only and are not intended as limitations on the scope of the present invention.

That which is claimed is:

1. A therapeutic method of treating the chronic human superficial fungus infection tinea pedis produced by the pathogenic dermatophytic fungi Microsporum sp., Trichophyton sp., and Epidermophyton sp., which invade and attack keratinized skin areas of the body comprising repeatedly applying topically to itching, macerated, cracked, and scaling skin areas of the body at the site of the infection, a fungicidally effective amount of a carrier antagonistic to the dermatophytic fungi, in order to exert at least an inhibitory growth effect upon the dermatophytes, the carrier including an antimicrobial organosilane having the general formula selected from the group consisting of

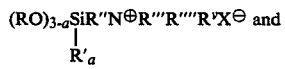 and

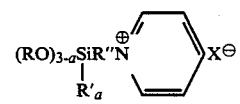

wherein, in each formula,
R is an alkyl radical of 1 to 4 carbon atoms or hydrogen;
a has a value of 0, 1 or 2;
R' is a methyl or ethyl radical;
R" is an alkylene group of 1 to 4 carbon atoms;
R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms; and
X is chloride, bromide, fluoride, iodide, acetate or tosylate.

2. The method of claim 1 wherein the carrier is selected from the group consisting of gels, powders, lotions, creams, emulsions, microemulsions, and solvent solutions of the organosilane.

3. The method of claim 2 wherein the carrier is a lotion and the lotion includes in addition to the organosilane each of talc, treithanolamine, propylene glycol, a suspension agent of a polymer of acrylic acid cross-linked with allyl sucrose, water, glyceryl stearate, lanolin alcohol, mineral oil, and stearic acid.

4. The method of claim 2 wherein the carrier is a lotion and the lotion includes in addition to the silane each of methyl cellulose, talc, propylene glycol, water, glyceryl stearate, lanolin alcohol, mineral oil, stearic acid, and a low viscosity fluid blend of polydimethylcyclosiloxanes.

5. The method of claim 3 wherein the organosilane is represented by the formula

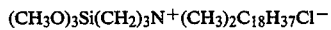

6. The method of claim 4 wherein the organosilane is represented by the formula

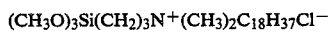

* * * * *